(12) United States Patent
Bonner et al.

(10) Patent No.: US 6,420,132 B1
(45) Date of Patent: Jul. 16, 2002

(54) PRECISION LASER CAPTURE MICRODISSECTION UTILIZING SHORT PULSE LENGTH

(75) Inventors: Robert F. Bonner, Washington, DC (US); Seth R. Goldstein, Bethesda, MD (US); Paul D. Smith, Annapolis, MD (US); Thomas J. Pohida, Monrovia, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/495,401

(22) Filed: Jan. 31, 2000

Related U.S. Application Data
(60) Provisional application No. 60/094,871, filed on Jul. 30, 1998.

(51) Int. Cl.⁷ .................................................. G01N 1/30
(52) U.S. Cl. ................................... 435/40.5; 435/40.52
(58) Field of Search ........................... 435/40.5, 40.52; 382/133; 428/346; 156/57

(56) References Cited

U.S. PATENT DOCUMENTS

| | | | |
|---|---|---|---|
| 4,624,915 A | | 11/1986 | Schindler et al. |
| 4,629,687 A | | 12/1986 | Schindler et al. |
| 5,202,230 A | | 4/1993 | Kamentsky |
| 5,541,064 A | | 7/1996 | Bacus et al. |
| 5,665,582 A | | 9/1997 | Kausch et al. |
| 5,723,290 A | | 3/1998 | Eberwine et al. |
| 5,759,781 A | | 6/1998 | Ward et al. |
| 5,817,462 A | | 10/1998 | Garini et al. |
| 5,843,644 A | | 12/1998 | Liotta et al. |
| 5,843,657 A | * | 12/1998 | Liotta et al. .................... 435/6 |
| 5,859,699 A | | 1/1999 | Baer et al. |
| 5,985,085 A | * | 11/1999 | Baer et al. .................. 156/285 |
| 6,100,051 A | * | 8/2000 | Goldstein et al. .......... 435/40.5 |
| 6,184,973 B1 | * | 2/2001 | Baer et al. ..................... 356/36 |
| 6,215,550 B1 | * | 4/2001 | Baer et al. ..................... 356/36 |
| 6,251,467 B1 | * | 6/2001 | Liotta et al. ................ 427/2.11 |
| 6,251,516 B1 | * | 6/2001 | Bonner et al. ............... 428/346 |

FOREIGN PATENT DOCUMENTS
| | | | |
|---|---|---|---|
| WO | WO 97/13838 | * | 4/1997 |

OTHER PUBLICATIONS
Bonner R. LCM. Science 278 1481, 1483 Nov. 21, 1997.*
Emmert–Buck M. LCM. Science 274 998–1001 Nov. 8, 1996.*

* cited by examiner

*Primary Examiner*—Ralph Gitomer
(74) *Attorney, Agent, or Firm*—William Michael Hynes; Townsend and Townsend and Crew LLP

(57) ABSTRACT

Laser capture microdissection occurs where the transfer polymer film is placed on a substrate overlying visualized and selected cellular material from a sample for extraction. The transfer polymer film is focally activated (melted) with a pulse brief enough to allow the melted volume to be confined to that polymer directly irradiated. This invention uses brief pulses to reduce the thermal diffusion into surrounding non-irradiated polymer, preventing it from being heated hot enough to melt while providing sufficient heat by direct absorption in the small focal volume directly irradiated by the focused laser beam. This method can be used both in previously disclosed contact LCM, non contact LCM, using either condenser-side (or beam passes through polymer before tissue) or epi-irradiation (or laser passes through tissue before polymer). It can be used in configuration in which laser passes through tissue before polymer with and without an additional rigid substrate. In its preferred configuration it uses the inertial confinement of the surrounding unmelted thermoplastic polymer (and the overlying rigid substrate) to force expansion of the melted polymer into the underlying tissue target. Utilizing the short pulse protocol, the targeted and extracted material can have a diameter equal to or smaller than the exciting beam.

20 Claims, 3 Drawing Sheets

PRECISION LASER CAPTURE MICRODISSECTION UTILIZING SHORT PULSE LENGTH

CROSS-REFERENCES TO RELATED APPLICATIONS

This application claims the benefit of U.S. Provisional Application Ser. No. 60/094,871, filed Jul. 30, 1998, which is incorporated herein by reference.

FIELD OF THE INVENTION

This invention relates to laser capture microdissection a technique wherein a specimen is visualized under a microscope and then overlaid with a layer of transfer material which when activated by a laser adheres to and extracts out specific targeted elements within the specimen for further processing. More particularly, this disclosure focuses on extracting out samples that are equal in size to or smaller than the activating laser beam. The purpose of this invention is to provide a method and apparatus for reliable microdissection of targets within tissue or other specimen samples, smaller than approximately 10 microns in diameter.

BACKGROUND OF THE INVENTION

In WO 97/13838 entitled Isolation of Cellular Material Under Microscopic Visualization published Apr. 17, 1997 the statement is made at page 20, line 24 the statement is made:

The size of the tissue transferred, depending upon the needs of the operator, can be varied by changing the diameter of the laser beam and pulse duration. Highly reproducible transfers in the 60 to 700 $\mu$m diameter range are easily attainable for procurement of small (100 $\mu$m to 1 mm) lesions without the encroachment of adjacent, non-neoplastic cells. In most basic and clinical research studies, procurement of several hundred to several thousand cells is necessary to provide sufficient genetic material for reliable amplification and statistically meaningful analysis. However, since laser beams can be focused to less than one cell diameter, transfers of targeted single cells or even parts thereof is thought possible under the practice of the invention.

In the Application that follows we set forth the solution to the transfer that "is thought possible" mentioned above.

Although the first microdissection patents described a rigid inert substrate to which the thermoplastic polymer was applied which could be used as a pressure plate, the original implementation of LCM employed a freestanding film that was applied to the surface of the tissue by gently pressing the film onto the sample. The film above the tissue section of interest was then heated by a 100-micron diameter beam and melted by pulses from a $CO_2$ laser. The length of the laser pulse (between 100 msec and 630 msec) was chosen so as to allow the irradiated film to come to a steady state temperature rise for sufficiently long times for the polymer to flow into the tissue and form a strong bond by replacing air voids within the desiccated sample. The 630 msec pulses typically used with this system were purposefully chosen to be that long to insure sufficient time after the steady state temperature was reached for the melted polymer (which remains molten until the end of the pulse) to reliably flow into the tissue during the laser pulse. In subsequent work it was shown that equivalent transfers could be achieved with this system and 100 msec pulses, although because of irregular spacing between the polymer surface and the tissue, transfer with 100 msec pulses were less reproducible than with the longer pulses. In practice with this LCM system, the objective was to heat the lower surface of the polymer to a little more than its melting point. The $CO_2$ laser delivered power levels were kept within a factor of two of the threshold power required (range of 25–50 mW delivered to a 100 $\mu$m spot on an EVA polymer film 100 $\mu$m thick). Thus the tissue captured by the melted polymer was typically exposed to peak temperatures of ~90–100 C for ~500 msec. Using this process damage to DNA, RNA, or proteins in the captured sample was not observed by subsequent molecular analysis.

Short pulses were avoided in LCM so as to insure adequate bond strength. Information from a number of manufacturers of EVA-based thermoplastic adhesives (e.g., hot glue) suggested that using EVA adhesives required maintaining molten joint under pressure for more than one second. In the original $CO_2$ laser LCM designs, the use of a pressure plate (transparent and non absorbing of the laser and visible light) was impractical because of the rarity and expense of materials that transmit $CO_2$ laser wavelengths (9–11 $\mu$m). Subsequently the introduction of strongly-absorbing near infrared (~0.8 $\mu$m) dyes soluble in the thermoplastic polymers allowed the transfer film to be focally melted by the pulsed infrared laser diodes (~0.8 $\mu$m) easily focused through transparent substrates to small diameters less than 10 $\mu$m in the absorbing thermoplastic film.

SUMMARY OF THE INVENTION

Laser capture microdissection occurs where the transfer polymer film is placed on a substrate overlying visualized and selected cellular material from a sample for extraction. The transfer polymer film is focally activated (melted) with a pulse brief enough to allow the melted volume to be confined to that polymer directly irradiated. This invention uses brief pulses to reduce the thermal diffusion into surrounding non-irradiated polymer, preventing it from being heated hot enough to melt while providing sufficient heat by direct absorption in the small focal volume directly irradiated by the focused laser beam. This method can be used both in previously disclosed contact LCM or non-contact LCM, using either condenser-side (or beam passes through polymer before tissue) or epi-irradiation (or laser passes through tissue before polymer). It can be used in configurations in which laser passes through tissue before polymer with and without an additional inert substrate. In its preferred configuration it uses the inertial or elastic confinement of the surrounding un-melted thermoplastic polymer (and the overlying attached substrate) to force expansion of the melted polymer into the underlying tissue target. Utilizing the short pulse protocol, the targeted and extracted material can have a diameter equal to or smaller than the exciting beam even as the optical diffraction limits are approached.

For even greater precision and localization, a series of short "subthreshold" pulses can be delivered to the same or immediately adjacent points to just contact specific targets within the laser beam (i.e., a target smaller than the laser beam diameter located in the center of the laser pulse). This utilizes the fact that when a volume of polymer is melted from top to bottom of the absorbing thermoplastic film by a laser pulse, it expands a proportional volume towards the tissue. This volume of polymer expansion can be matched to the volume of the desired target including the initial volume of separation between the polymer and the target either by estimation of average pulse parameters required to accomplish that capture with a single pulse or using a laser pulse roughly half that required for single pulse capture and delivering a series of pulses until a bond with the target is achieved.

The purpose of this invention to provide a method that allows reproducible LCM transfer region of less than 20 microns with greatest precision, maximal efficiency, and minimal duration of thermal transients in the target sample caused by contact with the molten thermoplastic polymer during the laser pulse and subsequently until it cools. We have found that a reliable method for obtaining smaller transfer spot sizes (less Man 10 microns in diameter) involves reducing the pulse width of the laser to less than 1 msec and adjusting the peak power of the laser. These pulse widths and powers minimize damage to the macromolecules in the tissue sample.

We note at the time of filing this application, that the contact and adhering of the activatable material to the sample creates an observable phenomena. The user can actually observe the desired adherence to the sample while adjusting pulse length and power to expand, contract, and even shape the areas of adhesion.

DETAILED DESCRIPTION OF THE SPECIFIC EMBODIMENTS

Figure 1A:
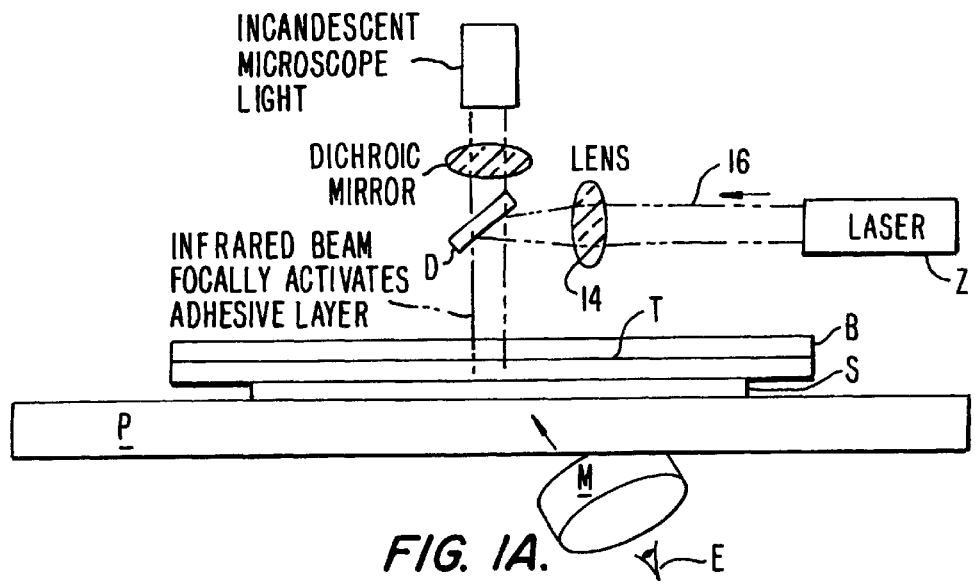
FIG. 1A is a schematic on laser capture microdissection in which the activating laser light passes through the condenser side of a microscope for the microdissection of selected tissue.

Referring to FIG. 1A, conventional contact LCM is illustrated. Referring to FIG. 1A, viewer at eye E visualizes specimen S on slide P through microscope M (schematically shown). Specimen S illumination occurs through incandescent microscope light L and dichroic mirror D. Illumination occurs through transparent backing B [which can be an inert, nonabsorbent layer either rigid or strong though flexible material such as polyester film—the former makes a rigid transfer element and the latter in combination with T a more flexible tape of 2 or more layers] and transparent transfer layer T.

Transfer layer T is typically a low temperature melting thermoplastic polymer with a large volume increase associated with the phase transition from a solid to a liquid (e.g., ethylene vinyl acetate) which can be dyed (e.g., at near-infrared wavelengths invisible to the eye) so as to couple to radiation 16 from laser Z of a specific frequency. When that part of specimen S is identified for LCM, laser Z is activated, and transfer layer T activated so as to adhere to specimen S at the selected tissue. Laser light 16 from laser Z passes through lens 14, onto dichroic mirror D and then through transparent backing plate B and onto transfer layer T.

Figure 1B:
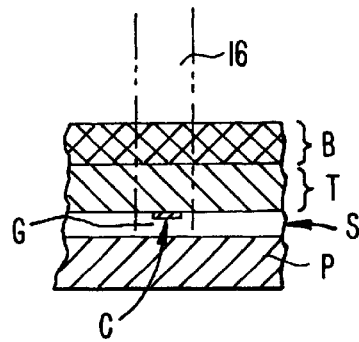
FIG. 1B is a detail at the site of the LCM illustrating the exciting laser beam and the capability of exciting an area smaller than the beam for more precisely targeting the contact LCM on selected tissue.

Turning to FIG. 1B, a detail of the illustrated contact LCM is illustrated. Laser beam 16 is illustrated passing through transparent backing B and into transfer layer T (which absorbs the beam but not visible light). Transfer layer T is here shown in contact with specimen S. It will be understood with reference to FIGS. 4A–4E that excitation of a smaller area of transfer layer T than the total exposed area of transfer layer T is possible. Therefore, adhering column C is shown protruding into specimen S to extract selected cell group G which can be as small as one cell.

In this LCM, it will be understood that transparent backing B has a function. Specifically, and by backing transfer layer T, transparent backing plate B forms an overlying substrate strong enough to resist expansion of the molten thermoplastic polymer. This overlying substrate combined with the inertial or elastic confinement of the surrounding inactivated material of transfer layer T forces the melted polymer to flow towards the tissue sample. The preferred requirements on this overlying substrate are that it 1) is transparent to both visible light required for microscopic visualization and the infrared laser used to activate the thermoplastic polymer, 2) has a high enough melting point so that the heat from the adjacent molten laser-absorbing thermoplastic polymer does not melt it, and 3) is stiff enough that it does not appreciably deform under the pressures caused by the expansion of the adjacent laser activated thermoplastic polymer [i.e., under these transient forces it appears to be a rigid body].

Figure 2B:
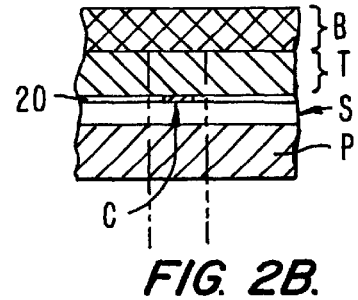
FIG. 2B is a detail at the site of the LCM illustrating the exciting laser beam and the capability of exciting an area smaller than the beam for more precisely targeting the non-contact LCM on selected tissue.
Figure 2A:
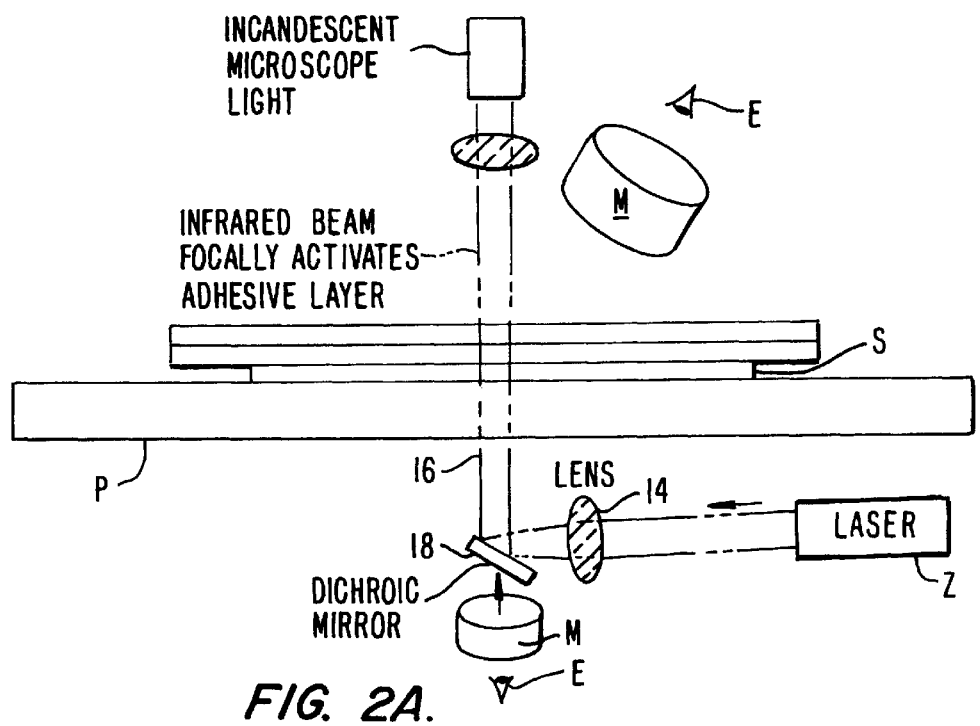
FIG. 2A is a schematic of non contact LCM, using either epi-irradiation (or laser passes through tissue before polymer) to cause the activated film to span to the selected tissue across a gap.

Having set forth generally the case of contact LCM, FIGS. 2A and 2B can illustrate the case of non-contact LCM.

FIG. 2A is essentially the same as FIG. 1A with the exception that a so-called epi-irradiation is utilized. Therefore, it will be seen that laser Z is below slide P.

Referring to FIG. 2B, it will be seen that laser beam 16 passes up through slide P, sample S, and spatial interval 20. Thereafter, laser beam 16 passes into transfer layer T for activation of the layer. As will hereafter be described, adhering column C spans this spatial interval 20 and again fastens to selected material G. Again, this fastening to selected material G consists of a column having diameter smaller than the true beam diameter. Thus, using the techniques hereafter described, the activated material may be "focused" relative to the laser beam 16 to actually occupy an area (or transfer target diameter) less than that of the laser beam (diameter) even when this beam diameter is reduced to less than 10 $\mu$m.

Figure 3:
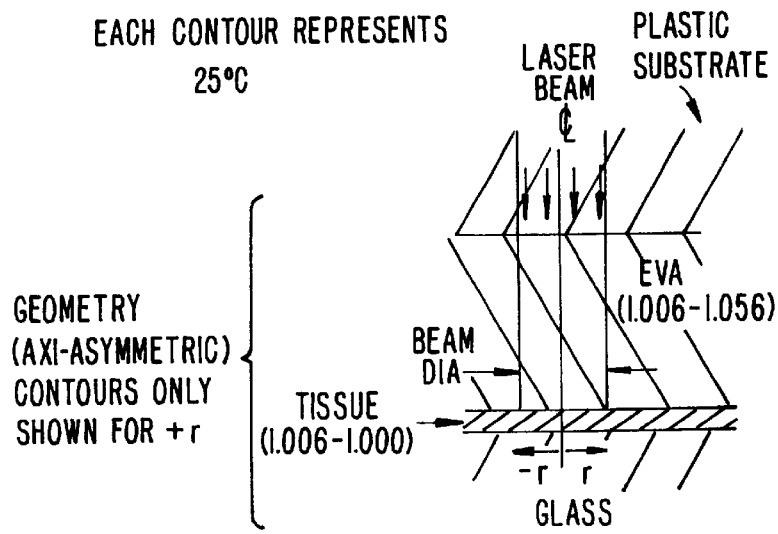
FIG. 3 is a view of a layer of EVA (ethylene vinyl acetate) with a beam passing through the layer.
Figures 4A, 4B:
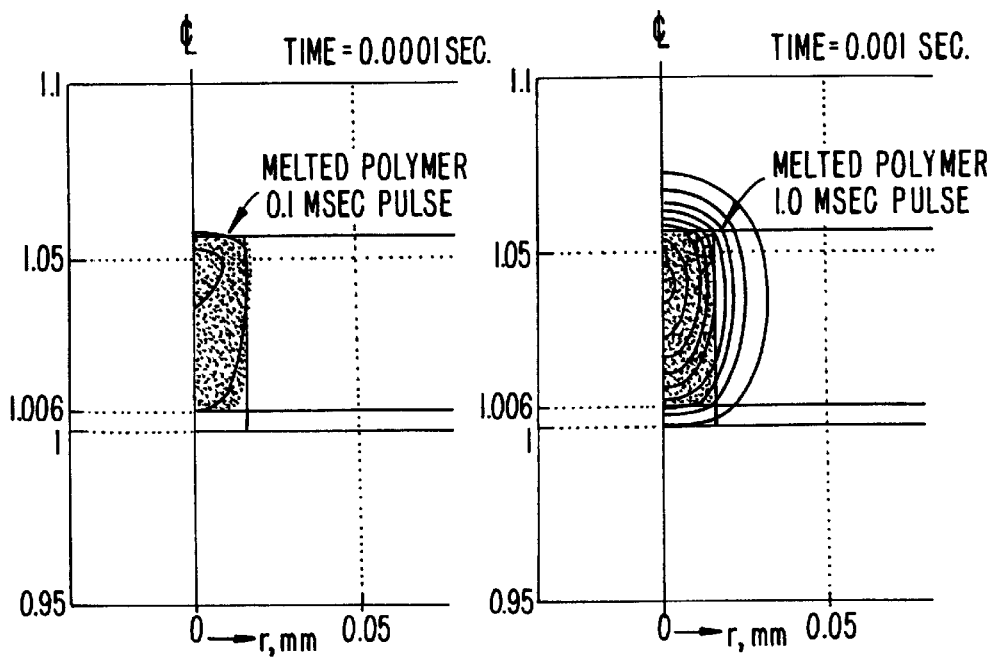
FIG. 4A–4E are successive radial profiles of the EVA of FIG. 3 illustrating the spreading of the radial profiles beyond the dimension of the beams with increasing duration of radiation, the contour interval increases with increasing laser beam power; it being understood that the 25° C. per contour for a 20 mW laser beam is shown (A 40 mW beam would produce 50° C. contour of identical shape.)
Figure 4C:
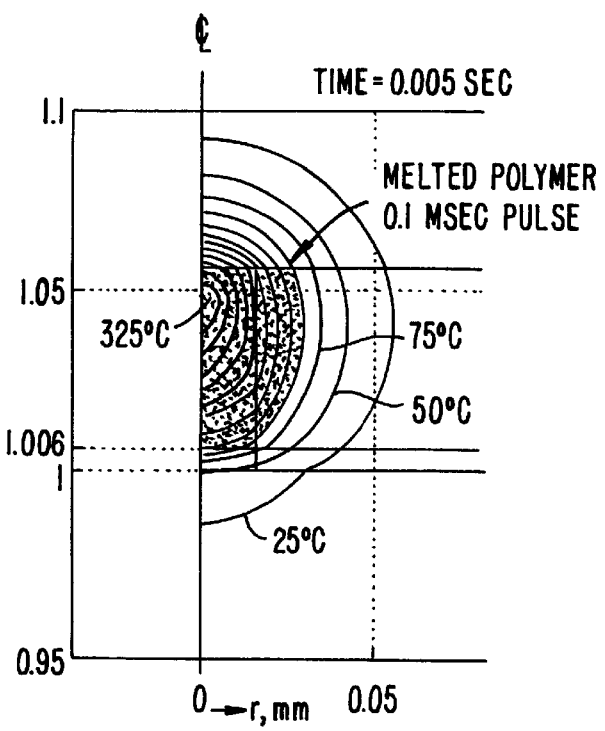
Figure 4D:
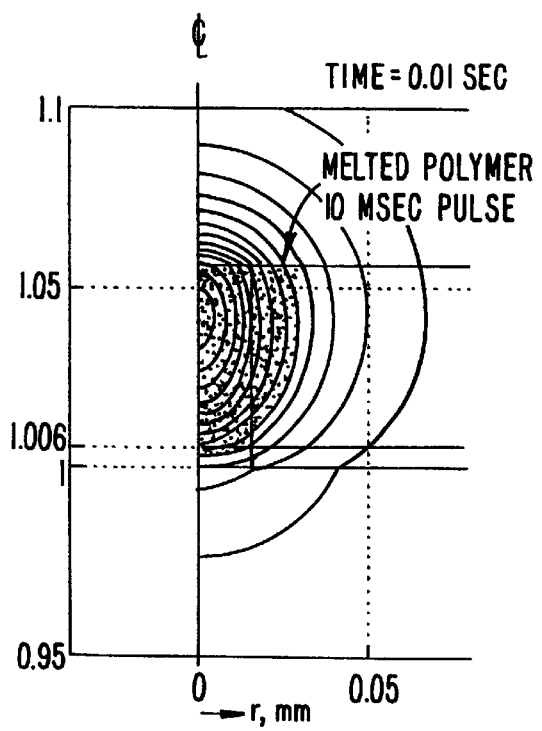
Figure 4E:
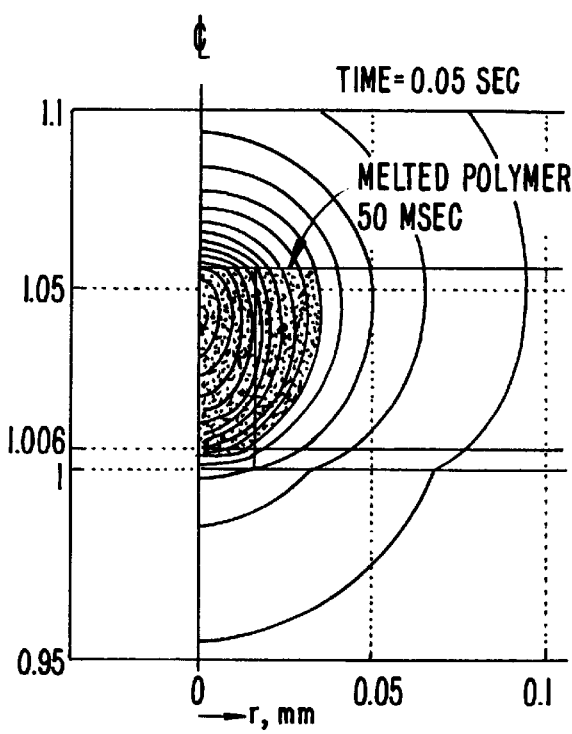

Referring to FIG. 3, a thermal model of temperature contours in polymer (EVA) which constitutes transfer layer T. It will be seen that overlying transfer layer T is transparent backing plate B. Underlying transfer layer T is glass slide P with specimen S. Beam diameter is 30 $\mu$m.

An important statement can be made relative to the darkened area appearing where the polymer is described as melted. The reader will understand that before contact is made between the melted film and the specimen at the selected portion, an air interface is present between the specimen and film. The air-sample interface is normally a highly irregular surface with a large index of refraction mismatch which strongly scatters light incident upon the sample.

When contact and adhesion of the melted thermoplastic polymer to the sample occurs, the index of refraction mismatch is strongly reduced (the polymer and sample have indices of refraction much more nearly the same than either with air) and consequently a clearly visible change in the transmission image of the sample at the point of contact occurs. Specifically, the scattering decreases and the contacted and adhered portion of the specimen becomes "brighter." Thus, as attachment to the melted transfer film occurs, an easily visible interface is present for the observer.

It is to be emphasized that this change of appearance will be present even where the film is already "in contact" with the specimen. In the usual case, the surface of the specimen is very irregular. Contact of the film with the specimen at the "high" points of an irregular surface still produces a very perceptible light scattering. When heating and adhesion occurs, the foot print of the bonding is relatively easy to observe. Thus in the disclosed process, the operator has the advantage of being able to observe the bonding as it occurs.

Utilizing this technique, spot size can be visually adjusted using the disclosure herein. For example, where precise dissection is required, the observer can visually ascertain that the spot never at any time becomes larger than the area selected. Alternatively, where the material desired from the sample is essentially isolated—either by spatial separation or by "harmless" material surrounding it, the area of contact may be expanded. In either event, the contact here described provides a valuable visual interface which guides the observer during the collection process.

The characteristic darkened areas which guide the sample collector during this microdissection are also illustrated with respect to FIG. 4.

In typical practice of LCM using near-IR absorbing polymer films with an OD of ~0.3 and a thickness of ~50 micron, the pulse duration required to approach steady state within the center of the laser irradiated spot are ~100 msec for 100 $\mu$m beams, ~40 msec for 60 $\mu$m beams, ~10 msec for 30 $\mu$m beams, ~1 msec for 10 $\mu$m beams and about 500 usec for a 5 $\mu$m beam.

Using a special LCM system capable of delivering high power near laser diode pulses as short as 200 $\mu$sec, we quantitatively demonstrated some novel features of operating with short pulses compared to the steady state pulses previously used with LCM, that are the subject of this invention.

For a 10 $\mu$m beam, pulses shorter than 1.0 msec result in an EVA response (expansion and bonding) that is dependent on the product of power times pulse duration (or total energy delivered). In this short pulse regime, efficiency of heating the polymer and forming a bond is optimal. At longer pulses, more total heat (or absorbed laser energy which is the product of pulse duration and absorbed power) must be supplied resulting in larger transfer sizes and larger integrals of temperature times time to which the molecules in the tissue are exposed [i.e., time at elevated temperatures]. In general, for pulse duration longer than this "short time" regime, reliable transfers will be larger and the macromolecular thermal transients will be longer. Similarly for 5 $\mu$m beams, laser pulses less than 0.5 msec will give equivalent transfers at equivalent total energy (the power and pulse duration required for "efficient" transfers vary as reciprocals of one another).

The length of the thermal transient experienced by macromolecules in the targeted tissue can be reduced by using shorter pulses resulting in the same peak temperatures. The size of the transferred tissue is determined by the diameter of the region of the film that is raised to a temperature sufficient to melt and fuse it with the tissue sample. For long pulses (i.e., in the steady state conditions described by Goldstein, et al. Applied Optics 37:7378, 1998), the transfer size is determined by the power of the laser beam and by the thermal characteristics (thermal capacity and diffusion) of the LCM transfer film. The table below summarizes the parameters for conventional steady state LCM with transfer size set equal to beam diameter (using a 40 $\mu$m thick polymer, 5 $\mu$m thick tissue section):

TABLE 1

Conventional LCM parameters used for 30–100 $\mu$m transfers.

| Beam diameter | Transfer Size | Laser power | Laser pulse duration |
|---|---|---|---|
| 30 $\mu$m | 30 $\mu$m | 15 mW | 25 msec* |
| 60 $\mu$m | 60 $\mu$m | 30 mW | 50 msec* |
| 100 $\mu$m | 100 $\mu$m | 40 mW | 100 msec* |

*greater than or equal to

For higher powers: the transfer size and the corresponding peak polymer temperatures increase. However, for increasing pulse widths above those indicated in Table 1, neither the diameter of the transferred spot nor the peak temperatures vary significantly with the pulse width. When the LCM transfer film is to attached to an inert substrate rather than using a freestanding film, it 1) the substrate acts as a pressure plate permitting a defined application force,
2) reproducibly defines the lower or tissue bonding surface of the activatable polymer relative to a non-activated surface and allows rigid body positioning precision,
3) it prevents polymer expansion across or along the rigid substrate surface, and in combination with the surrounding inactivated and therefore solid thermoplastic polymer film forces the melted polymer to expand in the direction of and into the underlying tissue which results in reproducible surface area of contact between polymer and tissue and a strong bond.

In other words, wherever the film is irradiated by the laser with sufficient absorbed power to melt it focally, the molten film seeks to expand [due to its thermal expansion coefficient and the volume increase associated with going from a solid to a liquid], but is confined by the stiffness of film carrier and the unheated portions of the film. Once the "bottom" surface of the activated polymer melts, the expansion forces the molten film downwards and into the tissue. Thus, the film need not be in direct contact with the target. The bottom surface of molten portion of the film is pushed out during the laser pulse, fuses or bonds with the microscopic target, and this target within the volume described by this zone of polymer expansion is captured or bonded to the film and its substrate. The combination of 1) short, small beam pulses, 2) the large expansion on melting of the selected polymers, and 3) the confinement of the expansion and redirection towards the target allow reliable capture of targets smaller than 10 $\mu$m. For longer pulses (as in the original CO2 case) the polymer could expand upwards as well as down and would flow by gravity or surface tension once the melted polymer made contact with the tissue (or surface wetting of the target). However for the shorter pulses to create effective bonds, we require a high local pressure to force the rapid flow of polymer into the target (whether initially in contact or not). The expansion of the melted polymer creates this pressure. If the melted volume is confined by rigid material on all sides except for the direction of the target, such bonds can be made in less than a msec and are quite strong. The backing (substrate layer) is particularly critical when using the "condenser-side" irradiation—the top of film will melt first before the surface and the initial expansion without a "confining" inert substrate would be in the direction away from the target and the pressure forcing flow in the direction of the tissue once the top-to-bottom melt occurs would be significantly reduced. Thus bonds without confinement of polymer expansion on the top surface would not be as strong or as reliably formed in short times.

As long as these bonds are stronger that the original bond between the target and the glass slide, the target will be transferred to the film surface and separated from adjacent elements on the slide once the substrate is separated from the slide [if non-targeted adjacent elements are contiguous and attached to those targeted their separation further requires that the strength of the attachment of untargeted elements to the glass slide exceeds the strength of their attachment to the targeted elements]. Typically a series of laser bonds are formed to accumulate a group of equivalent targets from the region of interest in the slide prior to the separation of substrate, its thermoplastic polymer layer, and captured targets from the slide and the remaining microscopic elements on it.

PREFERRED EMBODIMENT

We use any of the existing LCM samples or films with any viewing or irradiation geometry [e.g., condenser side irradiation or epi-irradiation]. The combination of 1) short, small beam pulses, 2) the large fractional expansion on melting of the selected polymers (e.g., ~10%), and 3) the confinement of the expansion and redirection towards the target allow reliable capture of targets smaller than 10 $\mu$m. For longer pulses (as in the original CO2 case) the polymer could expand upwards as well as down and would flow by gravity of surface tension once the melted polymer made contact with the tissue (porous target). We require shorter laser pulses at somewhat higher powers than in conventional LCM in order to confine the melted volume of the attached polymer to small beam diameters (<20 microns). For these shorter pulses we require a high local pressure to force the rapid flow of polymer into the target (whether initially in contact or not). The large expansion of the melted polymer creates this pressure. If the melted volume is confined by rigid material on all sides except for the direction of the target, such bonds can be made in less than a msec and are quite strong. The backing (substrate layer) is particularly critical when using the "condenser-side" irradiation. In this case, the top of film will melt first before the bottom surface and the initial expansion without a "confining" inert substrate would be in the direction away from the target. This fluid path to air on the top will substantially reduce the pressure forcing flow in the direction of the tissue once the top-to-bottom melt occurs. Thus bonds would not be as strong or as reliably formed in short times.

In contrast to conventional long pulse LCM, at pulse widths below 1 msec the film does not approach thermal equilibrium at distances more than 2 microns from the edge of the laser beam during the laser pulse. Consequently heat loss is minimized. Therefore, when suitable energy is delivered to and absorbed by the activatable layer, only the film in the region exposed to the laser heats to the melting point during the laser pulse, expanding to contact and fuse to the tissue. For a short pulse (less than 1 msec) there is insufficient time for the temperature of the film to increase to the melting point outside the region exposed to the laser pulse since the laser pulse is so short. This region remains below the melting point and does not fuse to the tissue. Thus, for short pulses the transfer region size is not increased by thermal diffusion and the tissue transfer size is .determined primarily by the laser spot diameter. For short pulses we observe that the transfer spot size increases as we increase the pulse width of the laser, in contrast to the longer pulse conventional LCM regime, indicating that we are operating in a different thermal diffusion regime. The table below summarizes the parameters for new short pulse LCM with transfer size equal to beam diameter (using a 40 $\mu$m thick polymer, 5 $\mu$m thick tissue section):

TABLE 2

Short Pulse LCM Parameters required for smallest size transfers (5 and 10 $\mu$m diameter of 5 $\mu$m thick targets

| Beam diameter Energy | Transfer Size | Laser power | Pulse duration | |
|---|---|---|---|---|
| 10 $\mu$m | 10 $\mu$m | 30 mW | 1 msec | 30 $\mu$J |
| 10 $\mu$m | 10 $\mu$m | 43 mW | 0.7 msec | 30 $\mu$J |
| 10 $\mu$m | 10 $\mu$m | 60 mW | 0.5 msec | 30 $\mu$J |
| 5 $\mu$m | 5 $\mu$m | 30 mW | 0.3 msec | 9 $\mu$J |
| 5 $\mu$m | 5 $\mu$m | 45 mW | 0.2 msec | 9 $\mu$J |
| 5 $\mu$m | 5 $\mu$m | 18 mW | 0.5 msec | 9 $\mu$J |

Importantly, the bonding of the EVA polymers (such as Dupont Elvax 200 W, 410, 205 W and 4310) to tissue is reliably obtained with strength sufficient to permit reproducible transfers in thermal transients as short as 0.3 msec. Thus not only can the molten polymer be confined to a few micron diameter region with short pulses, but reliable bonds to tissue can be made in such brief molten transients.

In Table 2 above, experimental measurements demonstrate equivalent transfers for the same pulse energy when the laser pulse duration is kept below a critical time associated with the time for significant thermal diffusion from the irradiated volume. As indicated, below a certain pulse length [<<1 msec for a 10 um diameter spot and 0.5 msec for a 5 um diameter spot], the laser energy required to create a given small transfer size is essentially constant (e.g., 9 micro-Joules for a 5 micron transfer using a 40 $\mu$m-thick activatable EVA film with an OD of 0.4 at the laser wavelength). In general preferred embodiments of LCM have used thermoplastic polymers (e.g., EVA's with low vinyl acetate percentage) with low melting temperature so that the peak temperature required to form a thermoplastic bond is minimized.

As can be seen from Table 2 above, in the short pulse regime utilized the laser energy required to create a given small transfer size is essentially constant (e.g., 9 micro Joules for a 5 micron transfer using a 40 $\mu$m-thick activatable EVA film with an OD of 0.4 at the laser wavelength). Although any of these pulses may be used to capture an equivalent-sized microscopic element, there are some inherent physical differences that suggest specific optimization strategies. In general, the shorter higher power pulses [e.g., 5 $\mu$m, 45 mW and 0.2 msec with 9 micro-joules] create higher peak temperatures within the thermoplastic polymer than that of the longer equivalent pulses [e.g., 5 $\mu$m, 18 mW and 0.5 msec also with 9 micro-joules]. Increasing temperatures within the molten polymer create lower transient viscosity and could cause more effective injection of polymer into the finest voids within the target volume. However, shorter higher power pulses will also be associated with higher peak thermal transients in the captured targets during the brief period between the instant the molten polymer first contacts the target and when the polymer cools and solidifies (after the end of the pulse and rapid cooling by heat flow through the underlying glass). On the other hand the slightly longer, lower power pulses cause the same maximal volume of molten polymer and volume expansion with the same absorbed energy doing so with lower peak temperatures and longer times which may minimize peak thermal insult to the sample while allowing longer times to create a strong mechanical bond with the target. In general preferred embodiments of LCM have used thermoplastic polymers (e.g., EVA's with low vinyl acetate percentage) with low melting temperature so that the peak temperature required to form a thermoplastic bond are minimized. When working with thermally sensitive materials such as proteins for which preservation of enzyme function is required, the preferred "equivalent" laser parameters in Table 2 are the longest efficient pulses listed.

Required for successful bonding of the target are 1) melting along the laser beam axis of the activatable polymer from top to bottom surface and 2) expansion of the thermoplastic polymer on this axis to the target surface and within target void spaces. Previous LCM utilizes longer pulses capable of achieving steady state temperature distributions within the melted polymer and used polymer thickness roughly equal to the laser beam diameter (Table 1:30–100 um). When using short pulses that minimize lateral thermal diffusion in order to enable smaller target transfers, heat flow from the top to bottom of the film during the laser pulse is also reduced. The laser-induced thermal gradient from the top to bottom of the irradiated volume increases with both thickness of the activatable polymer and its optical density (absorbance) at the activating laser wavelength. Thus particularly for short pulse LCM the activatable polymer film must be carefully designed with respect to thickness and optical density. As previously described (Bonner et al., Science 278:1431, 1997 and patents . . . ), the absorbance of thermoplastic polymers such as ethylene vinyl acetate at near-IR laser wavelengths can be precisely controlled by the concentration of added strong near-IR absorbing molecules such as naphthalocyanine dyes which are highly soluble in the polymer. The absorbance of the thermoplastic film at the laser wavelengths used should be held to OD<0,43 by varying the dye concentration with film thickness to be used. Additionally thinner films when melted from top to bottom in small spots are associated with respectively smaller volumes of melted polymer and therefore smaller polymer expansion volumes. Thus the thinner polymer films will have intrinsically greater precision of capture—particularly for thinner target specimens. On the other hand, when either the initial separation gap between the un-activated polymer surface and the target surface or the target thickness increases, the required expansion distance to create an effective bond and associated transfer also increases. In such cases the polymer thickness will have to be increased and the dye concentration reduced.

An additional preferred embodiment uses the short pulse LCM method at slightly lower powers (within a factor of two of the power necessary to transfer an object in the specimen exactly equal to the beam size with a single pulse), but with a series of pulses (at a repetition of <<2–3 pulses per second). This series of pulses increment the forward motion of the extension of the polymer until it just contacts and bonds to a target cell or microscopic object on the slide at which point the pulse train is stopped. In this process, the first short pulse causes the polymer to focally melt and be forced outward from the surface by the combination of thermal expansion and inertial and elastic confinement of the surrounding solid materials. Since the individual pulse is short and the cooling/solidification of the small extension is very rapid (<<1 msec), after brief cooling a solid small pedestal has been formed extending from the polymer surface. Each additional pulse will extend the polymer in progressively smaller increments toward the target. In this way the smallest possible transfers can be made reliably by giving just the number of pulses necessary to extend the polymer to tissue contact. Additional pulses after contact allow the expansion of the polymer into the tissue up to the size of the laser beam.

Since under microscopic observation during LCM an optical brightening of the target region is observed due to index matching of the tissue surface by the contacting polymer, the first pulse that makes contact with the tissue can be readily determined. In this manner transfer may be reliably made at a scale that is less than the actual beam size (e.g., it is possible to target and transfer ~1 micron objects with a 5 micron beam).

A third preferred short pulse LCM method, uses additional multiple supra threshold pulses after first contact with the target sample to allow a whole, irregularly shaped single cell (target object within the sample) to be captured using a beam that is slightly smaller than the single cell. Since the polymer flows within the porous desiccated tissue, with short pulses near threshold the polymer preferentially flows along contiguous macromolecular structures within a given cell and tends to fill that cell completely before expanding across intercellular borders. In this way short near threshold pulses are capable of targeting individual cells or densely connected structures such as a cell nucleus even when they are irregularly shaped and not congruent with the laser beam shape.

The precision of short-pulse LCM or the minimal size of the captured element described here is for dense specimens such as a tissue section in which desired targets are immediately contiguous with unwanted ones. It is understood that even greater precision can be achieved when capturing smaller particles separated more widely that their diameters (e.g., a dilute cytology cell smear or chromosome squash). In this case, smaller pure targeted elements can be captured by polymer expansion that encompasses the elements and surrounding void space on the microscope slide without bonding to the nearest unwanted element. Thus elements as small as 1 $\mu$m might be microscopically targeted and captured with great purity (e.g., by the 5 um laser pulses in Table 2). Although it might be thought that the ultimate resolution of LCM capture is limited by the wavelength of both the light used for microscopic visualization and targeting and the activating laser, there are circumstances in which submicron particles might be targeted and captured [i.e., purified from a complex mixture] with this technique. For example specific fluorescence markers might identify specific submicron particles without resolving their structure. If these particles are spread at low enough density on the microscope slide (mean separation approximately 5 um), the short pulse LCM could target and capture them. Furthermore the after transfer images of the remaining specimen slide and of the transfer surface can verify and quantify the capture process.

We have described the above LCM technique with respect to biological applications. It should be understood that these techniques are applicable to any sample which are microscopically observable. For example, a heterogenous collection of elements in which the method effects a separation of a microscopically distinguishable component or collection of components can work as well. Thus, a microscope based separation method using a selectively activated transfer film applied to tissue, cytology specimens, cellular organelles, chromosomes, viruses, is disclosed. Additionally, non living objects identifiable by microscopy into subsets to be isolated using LCM methods can be separated as well.

U.S. patent application Ser. No. 08/883,821 entitled Convex Geometry Adhesive Film System for Laser Capture Microdissection now U.S. Pat. No. 6,100,051 issued Aug. 8, 2000 is incorporated herein by reference. In this disclosure, the use of a convex surface having a selectively activatable adhesive for the side-by-side collection and concentration of specimens gathered by laser capture microdissection is set forth. The reader will understand, in this disclosure we set forth collection of extremely small or rare elements by laser capture microdissection. The combination of these two disclosures permits the isolation and collection of specific very small elements in a group from a microscopic specimen. Thereafter, transfer of the collected groups can occur to any precise place for further analysis.

What is claimed is:

1. In a method of direct extraction of material from a sample which comprises the steps of:
    providing a sample;
    providing a transfer film which only upon activation at selected regions has a property to provide the selected regions thereof with characteristics adhesive to the sample;
    juxtaposing the sample with the transfer film to maintain a small separation between the transfer film and the sample;
    identifying at least one portion of material for extraction from the sample;
    directing a brief pulsed radiation beam of a preselected beam diameter and preselected pulse length onto the transfer film to activate a volume within the transfer film adjacent to the sample so that an activated portion dependent upon pulse duration of the transfer film equal to or less than the preselected beam diameter spans the small separation and adheres to the at least one portion of material of the sample;
    separating the transfer film from the sample while maintaining adhesion between the transfer film and the at least one portion of material of the sample so that the at least one portion of material of the sample is extracted from a remaining portion of the sample.

2. A method of direct extraction of material from a sample according to claim 1 and further including:
    the step of providing a transfer film includes providing a thermoplastic polymer with a large volume expansion associated with melting in order to create expansion and a driving force sufficient to force and bond the melted polymer onto and into the at least one portion of the material of the sample.

3. A method of direct extraction of material from a sample according to claim 2 and further including:
    the step of providing a transfer film includes providing an inert backing substrate on the top surface of the thermoplastic polymer which prevents the large volume expansion associated with melting from moving away from the desired target but rather causes the internal pressure created by the expanding polymer to force and bond the melted polymer onto and into the at least one portion of the material of the sample.

4. A method of direct extraction of material from a sample according to claim 1 and further including:
    observing an optical interface between the sample and the transfer film during the directing step to determine the spatial extent that the at least one portion of the material of the sample adheres to the transfer film.

5. A method of direct extraction of material from a sample according to claim 1 and further including:
    increasing the preselected pulse length to increase the activated area of the transfer film.

6. A method of direct extraction of material from a sample according to claim 1 and further including:
    decreasing the preselected pulse length to decrease the activated area of the transfer film.

7. In the method of direct extraction of material according to claim 6 wherein:
    delivering additional pulses after the first pulse which creates a bond in order to incrementally increase the diameter of the bonded region to a desired target.

8. A method of direct extraction of material from a sample according to claim 1 and further including:
    the sample is a biological sample and the at least one portion of the sample is selected from the group consisting of tissue, cytology specimens, cellular organelles, chromosomes, and viruses.

9. A method of direct extraction of material from a sample according to claim 1 and further including:
    the sample is nonliving objects identifiable by microscopy and the at least one portion of the sample is an identifiable subset of nonliving objects identifiable by microscopy.

10. In a method of direct extraction of material from a sample which comprises the steps of:
    providing a sample;
    providing a transfer film which only upon activation at selected regions has a property to provide the selected regions thereof with characteristics adhesive to the sample;
    juxtaposing the sample with the transfer film to maintain a small separation between the transfer film and the sample;
    identifying at least one portion of material of the sample which is to be extracted;
    directing a beam of a preselected beam diameter onto the transfer film melts to melt a selected area/region of the film, span the small separation, and forms a bond to activate the transfer film so that an activated area of the transfer film adheres to the at least one portion of material of the sample; and,
    separating the transfer film from the sample while maintaining adhesion between the transfer film and the at least one portion of material of the sample so that the at least one portion of material is extracted from a remaining portion of the sample;
    the improvement to the method where the step of directing a beam of preselected beam diameter onto the transfer film includes:
    pulsing the directed beam to activate a volume of the transfer film having the preselected beam diameter to induce adherence to the at least one portion of material of the sample; and
    observing an optical interface between the sample and the transfer film during the directing step to determine the spatial extent that the at least one portion of the material of the sample adheres to the transfer film.

11. In the method of direct extraction of material according to claim 10 wherein:
    adjusting the pulse duration to activate an area of the transfer film equal to or smaller than the preselected beam diameter for adherence to the at least one portion of material of the sample.

12. In the method of direct extraction of material according to claim 10 wherein:

lowering the pulse energy so that a single subthreshold pulse is just insufficient to activate the transfer film to any point on the sample; and, delivering a series of such subthreshold pulses to the transfer film in juxtaposition but not in contact with the at least one portion of material to be extracted until the transfer film bonds to the at least one portion of material to be extracted.

13. In the method of direct extraction of material according to claim 12 wherein:

lowering the pulse energy by decreasing pulse length.

14. In the method of direct extraction of material according to claim 12 wherein:

lowering the pulse energy by decreasing pulse power.

15. In a method of direct extraction of material from a sample which comprises the steps of:

providing a sample;

providing a transfer film which only upon activation at selected regions has a property to provide the selected regions thereof with characteristics adhesive to the sample;

providing a backing on a side of the transfer film away from the sample;

juxtaposing the sample to the transfer film on the other side of the transfer film to maintain a small separation between the transfer film and the sample;

identifying at least one portion of material for extraction from the sample;

directing a pulsed radiation beam of a preselected beam diameter and preselected pulse length onto the transfer film to activate a volume within the transfer film adjacent to The sample so that the activated volume on a side of the transfer film adjacent the backing moves an area of the transfer film equal to or less than the preselected beam diameter to span the small separation and move into adherence to the at least one portion of material of the sample;

separating the transfer film from the sample while maintaining adhesion between the transfer film and the at least one portion of material of the sample so that the at least one portion of material of the sample is extracted from a remaining portion of the sample.

16. In a method of direct extraction of material from a sample according to claim 15 and wherein:

observing an optical interface between the sample and the transfer film during the directing step to determine the spatial extent that the at least one portion of the material of the sample adheres to the transfer film.

17. In a method of direct extraction of material from a sample according to claim 15 and wherein:

juxtaposing the sample to the transfer film includes contacting the sample with the transfer film.

18. In a method of direct extraction of material from a sample according to claim 15 and wherein:

juxtaposing the sample to the transfer film includes having the transfer film at a spatial interval from the sample.

19. A method of direct extraction of material from a sample comprising the steps of:

providing a sample;

providing a transfer film which only upon activation at selected regions has a property to provide the selected regions thereof with characteristics adhesive to the sample;

juxtaposing the sample with the transfer film so that the transfer film is at a small interval from the sample;

identifying at least one portion of material for extraction from the sample;

directing a pulsed radiation beam of a preselected beam diameter and preselected pulse length onto the transfer film to activate a volume within the transfer film adjacent to the sample so that an activated area of the transfer film equal to or less than the preselected beam diameter progressively advances to and contacts only the at least one portion of material of the sample;

observing the contact between the transfer film and the at least one portion of material of the sample;

directing a further pulsed radiation beam onto the contact at the sample to cause adhesion only between the transfer film mad the sample; and, separating the transfer film from the sample while maintaining adhesion between the transfer film and the at least one portion of material of the sample so that the at least one portion of material of the sample is extracted from a remaining portion of the sample.

20. In a method of direct extraction of material from a sample according to claim 19 and including:

directing a still further pulsed radiation beam onto the contact at the sample to expand the area of the adhesion between the transfer film and the sample.

* * * * *